United States Patent [19]

Lohmann et al.

[11] Patent Number: 5,719,139
[45] Date of Patent: Feb. 17, 1998

[54] 9-OXO-1-AZABICYCLO[5.2.0]NON-2,4-DIENE-2-CARBOXYLIC ACID COMPOUNDS AS ANTIBIOTICS

[75] Inventors: Jean-Jacques Marcel Lohmann, Merfy; Patrice Jacky Daniel Koza, Sillery, both of France

[73] Assignees: Zeneca Limited, London, United Kingdom; Zeneca Pharma SA, Cergy Cedex, France

[21] Appl. No.: 587,903

[22] Filed: Jan. 16, 1996

[30] Foreign Application Priority Data

Jan. 18, 1995 [EP] European Pat. Off. ............. 95400094

[51] Int. Cl.$^6$ ................. C07D 487/04; C07D 223/00; A61K 31/55
[52] U.S. Cl. ............................ 514/210; 540/204
[58] Field of Search ......................... 540/204; 514/210

[56] References Cited

FOREIGN PATENT DOCUMENTS 0045198   2/1982   European Pat. Off. .

OTHER PUBLICATIONS

Mori et al., An Efficient Synthesis of Bicyclic β–Lactams through Palladium Catalysed Ene–Halogenocyclization, J. Chem. Soc., Chem. Commun., 1986, pp. 1375–1376.

Mori et al., Formation of Three–membered Rings from γ–Iodoketones and γ–Iodoesters via 13–Elimination, J. Chem. Soc., Chem. Commun., 1988, pp. 12–14.

Abstract No. 30806, Chemical Abstracts, Feb. 1981, vol. 94, No. 5.

Helv. Chim. Acta. 1972, 55, pp. 2567–2572.

Morin et al., Rearrangement of Exomethylenecephams to Homocephams, Heterocycles, 1990, vol. 31, No. 8, pp. 1423–1426.

Brooks et al., Nuclear Modification of Clavulanic Acid. The Preparation of Two 4,7–Fused β–Lactam Systems, J. Chem. Soc. Perkin Trans. I, 1983, pp. 115–120.

Spry, C(2)–Spiroepoxy–Cephems, Tetrahedron Letters, 1978, pp. 4751–4754.

Baldwin et al., Enzymic Conversion of Deuterated Analogues of δ–L–α–Aminoadipoly–L–Cysteinyl– D–Allylglycine, An Unnatural Substrate For Isopenicillin N Synthase: A Unified Theory of Second Ring Closure, Tetrahedron, 1991, vol. 47, No. 38, pp. 8223–8242.

Hirai et al., Acid–Catalyzed Rearrangement of α–Aminoalkylidene–β–alkoxy β–Lactams, J. Org. Chem., 1980, 45, pp. 936–942.

*Primary Examiner*—Mukund J. Shah
*Assistant Examiner*—Deepak Rao
*Attorney, Agent, or Firm*—Cushman Darby & Cushman Intellectual Property Group of Pillsbury Madison & Sutro, LLP

[57] ABSTRACT

The present invention provides a compound of the formula (I):

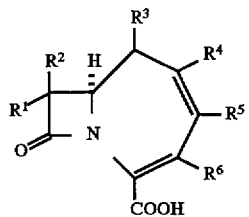

wherein $R^1$ is hydrogen, optionally substituted; acylamino, $C_{1-6}$alkyl, $C_{2-6}$alkenyl, $C_{2-6}$alkynyl, $C_{1-6}$alkoxy, $C_{1-6}$alkanoyloxy, $C_{1-6}$alkylamino, di-($C_{1-6}$alkyl)amino, $C_{1-6}$alkoxycarbonyl, aminocarbonyl, $C_{1-6}$alkylaminocarbonyl or di-($C_{1-6}$alkyl) aminocarbonyl;

$R^2$ is hydrogen or $C_{1-6}$alkoxy; or $R^1$ and $R^2$ together form optionally substituted $C_{1-6}$alkylene;

$R^3$ and $R^5$ are independently hydrogen or $C_{1-6}$alkyl; and one of $R^4$ and $R^6$ is hydrogen or $C_{1-4}$alkyl and the other is selected from a number of groups or a pharmaceutically acceptable salt or in vivo hydrolysable ester thereof.

Processes of their preparation, intermediates in their preparation, their use as therapeutic agents and pharmaceutical compositions containing them.

14 Claims, No Drawings

9-OXO-1-AZABICYCLO[5.2.0]NON-2,4-DIENE-2-CARBOXYLIC ACID COMPOUNDS AS ANTIBIOTICS

The invention relates to 9-oxo-1-azabicyclo[5.2.0]non-2,4-diene-2-carboxylic acid compounds, to processes for their preparation, to intermediates in their preparation, to their use as therapeutic agents and to pharmaceutical compositions containing them.

The compounds of this invention are β-lactam antibiotics and can be used in the treatment of any disease that is conventionally treated with antibiotics for example in the treatment of bacterial infection in mammals including humans.

Known classes of β-lactam antibacterial compound include cephalosporins, carbacephems, oxacephems, carbapenems and penems. Prior to this discovery, the ring systems of the present invention were not known to possess antibacterial properties.

The compounds referred to herein are named in accordance with the following nomenclature:

Accordingly the present invention provides a compound of the formula (I):

wherein
R$^1$ is hydrogen, optionally substituted: acylamino, C$_{1-6}$alkyl, C$_{2-6}$alkenyl, C$_{2-6}$alkynyl, C$_{1-6}$alkoxy, C$_{1-6}$alkanoyloxy, C$_{1-6}$alkylamino, di-(C$_{1-6}$alkyl)amino, C$_{1-6}$alkoxycarbonyl, aminocarbonyl, C$_{1-6}$alkylaminocarbonyl or di-(C$_{1-6}$alkyl)aminocarbonyl;

R$^2$ is hydrogen or C$_{1-6}$alkoxy;

or R$^1$ and R$^2$ together form optionally substituted C$_{1-6}$alkylene;

R$^3$ and R$^5$ are independently hydrogen or C$_{1-6}$alkyl; and one of R$^4$ and R$^6$ is hydrogen or C$_{1-4}$alkyl and the other is selected from hydrogen, cyano, C$_{1-4}$alkylcarbonyl, C$_{1-4}$alkoxycarbonyl, benzoyl, C$_{1-4}$alkylsulphonyl, benzylsulphonyl, nitro, chloro, bromo, optionally substituted C$_{1-10}$alkyl, optionally substituted aryl, a group of the formula —SR$^7$; wherein R$^7$ is optionally substituted: C$_{1-10}$alkyl, C$_{2-6}$alkenyl, C$_{2-6}$alkynyl, C$_{3-10}$cycloalkyl, C$_{3-10}$cycloalkylC$_{1-3}$alkyl, aryl, arylC$_{1-3}$alkyl, heterocyclyl, heterocyclylC$_{1-3}$alkyl, heteroaryl or heteroarylC$_{1-3}$alkyl;

or one of R$^4$ and R$^6$ is hydrogen or C$_{1-4}$alkyl and the other is of the formula —OR$^{18}$, wherein R$^{18}$ is hydrogen, optionally substituted:

C$_{1-6}$alkyl, aryl, C$_{1-6}$alkanoyl or arylcarbonyl;

or one of R$^4$ and R$^6$ is hydrogen or C$_{1-4}$alkyl and the other is of the formula —N(R$^{19}$)R$^{20}$ wherein R$^{19}$ and R$^{20}$ are independently hydrogen, optionally substituted C$_{1-6}$alkyl, C$_{1-6}$alkanoyl, arylC$_{1-3}$alkanoyl, arylcarbonyl, heterocyclyl, heterocyclylC$_{1-3}$alkyl, heteroaryl, heteroarylC$_{1-3}$alkyl, arylC$_{1-3}$alkyl, cycloalkyl or cycloalkylC$_{1-3}$alkyl;

or one of R$^4$ and R$^6$ is hydrogen or C$_{1-4}$alkyl and the other is of the formula —CH$_2$R$^{21}$ wherein R$^{21}$ is aryl or of the formula —SR$^7$, —OR$^{18}$ or —N(R$^{19}$)R$^{20}$ wherein R$^7$ and R$^{18}$-R$^{20}$ are as hereinabove defined;

or a pharmaceutically acceptable salt or in vivo hydrolysable ester thereof.

Suitable substituents for carbon atoms in optionally substituted R$^1$ and R$^2$ groups include, halo, hydroxy, amino, C$_{1-4}$alkoxy, cyano, nitro, C$_{1-4}$alkyl, C$_{1-4}$alkylthio, C$_{1-4}$alkanoyl, carboxy, C$_{1-4}$alkoxycarbonyl, C$_{1-4}$alkylsulphinyl, C$_{1-4}$alkylsulphonyl, triazolyl and tetrazolyl.

Suitable substituents for optionally substituted R$^4$ and R$^6$ groups include hydroxy, halo, C$_{1-4}$alkoxy, cyano, amino, C$_{1-6}$alkylamino, di-(C$_{1-6}$alkyl)amino, C$_{1-6}$alkanoylamino, C$_{1-4}$alkoxycarbonyl, carboxy, iminoC$_{1-6}$alkyl, C$_{1-6}$alkyliminoC$_{1-4}$alkyl, iminomethyl, C$_{1-6}$alkylimino, C$_{1-6}$alkylthio, C$_{1-6}$alkylsulphinyl, C$_{1-6}$alkylsulphonyl, arylC$_{1-4}$alkanoyl, aryloxyalkanoyl, oxo, a group of the formula —N=C(R$^8$)R$^9$, —N(R$^{10}$)C(R$^{11}$)=NR$^{12}$, —C(N(R$^{13}$)R$^{14}$)=NR$^{15}$, —CON(R$^{16}$)R$^{17}$ wherein R$^8$ is amino, C$_{1-4}$alkylamino or di-(C$_{1-4}$alkyl)amino;

R$^9$–R$^{15}$ are independently hydrogen or C$_{1-4}$alkyl;

R$^{16}$ is hydrogen or C$_{1-4}$alkyl;

R$^{17}$ is hydrogen, C$_{1-4}$alkyl, aryl, heteroaryl, heterocyclyl, cycloalkyl or cycloalkylC$_{1-3}$alkyl.

Preferably R$^1$ is alkyl optionally substituted by halo, hydroxy, C$_{1-6}$alkylthio, C$_{1-6}$alkanoyl, C$_{1-6}$alkylsulphinyl, C$_{1-6}$alkylsulphonyl, triazolyl, tetrazolyl or acylamino. Most preferably R$^1$ is C$_{1-4}$alkyl optionally substituted by halo or hydroxy or of the formula R$^{50}$—C(=N—OR$^{51}$)—, wherein R$^{50}$ and R$^{51}$ are as hereinbelow defined.

In particular R$^1$ is 1-hydroxyethyl, 1-fluoroethyl or hydroxymethyl.

In another aspect R$^1$ is 2-(2-aminothiazol-4-yl)-2-(1-carboxy-1-methylethoxyimino)acetamido.

Preferably R$^2$ is hydrogen.
Preferably R$^3$ is hydrogen or methyl.
Preferably R$^5$ is hydrogen.
Preferably one of R$^4$ and R$^6$ is hydrogen and the other is hydrogen, optionally substituted C$_{1-10}$alkyl, optionally substituted aryl, a group of the formula —S(O)$_n$R$^7$ wherein n is 0, 1 or 2 and R$^7$ is optionally substituted: C$_{1-6}$alkyl or heterocyclyl wherein optional substituents on C$_{1-6}$alkyl are selected from amino, C$_{1-4}$alkylamino, di-(C$_{1-4}$alkyl)amino or of the formula: —N=C(R$^8$)R$^9$, —N(R$^{10}$)C(R$^{11}$)=N—R$^{12}$ and —C(N(R$^{13}$)R$^{14}$)=N—R$^{15}$ wherein R$^8$-R$^{15}$ are as hereinabove defined and optional substituents on heterocyclyl groups are selected from C$_{1-4}$alkyl, carboxy, C$_{1-4}$alkoxy, carbonyl, —CON(R$^{16}$)R$^{17}$ wherein R$^{16}$ and R$^{17}$ are as hereinabove defined; of the formula —OR$^{18}$ wherein R$^{18}$ is as hereinabove defined; of the formula —N(R$^{19}$)R$^{20}$ wherein R$^{19}$ and R$^{20}$ are independently selected from hydrogen, C$_{1-4}$alkyl, C$_{1-4}$alkanoyl and aryl; or of the formula —CH$_2$R$^{21}$ wherein R$^{21}$ is as hereinabove defined.

In particular, one of R$^4$ and R$^6$ is of the formula —SR$^7$.

In particular, $R^7$ is of the formula

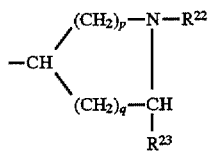

wherein p is 1 or 2, q is 1 or 2, $R^{22}$ is hydrogen or $C_{1-4}$alkyl and $R^{23}$ is hydrogen, carboxy, $C_{1-4}$alkoxycarbonyl, —CON($R^{16}$)$R^{17}$ wherein $R^{16}$ and $R^{17}$ are independently hydrogen, $C_{1-4}$alkyl, phenyl or thienyl. In particular, when $R^{16}$ or $R^{17}$ is phenyl or thienyl, the phenyl or thienyl group is substituted by at least one carboxy substituent.

In another aspect, one of $R^4$ and $R^6$ is of the formula —S(O)$_n$R$^7$ wherein n is 0 or 2 and $R^7$ is optionally substituted $C_{1-6}$alkyl.

Most preferably one of $R^4$ and $R^6$ is $C_{1-4}$alkanoyloxy or of the formula —S(O)$_n$R$^7$ wherein n is 0 or 2 and $R^7$ is $C_{1-6}$alkyl optionally substituted by amino or one of $R^4$ and $R^6$ is of the formula —SR$^7$ wherein $R^7$ is of the formula:

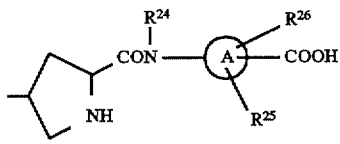

wherein $R^{24}$ is hydrogen or $C_{1-4}$alkyl and A is a phenyl or thienyl ring; and $R^{25}$ and $R^{26}$ are the same or different and are selected from hydrogen, halo, cyano, $C_{1-4}$alkyl, nitro, hydroxy, carboxy, $C_{1-4}$alkoxy, $C_{1-4}$alkoxycarbonyl, aminosulphonyl, $C_{1-4}$alkylaminosulphonyl, di-$C_{1-4}$-alkylaminosulphonyl, carbamoyl, $C_{1-4}$alkylcarbamoyl, di-$C_{1-4}$alkylcarbamoyl, trifluoromethyl, sulphonic acid, amino, $C_{1-4}$alkylamino, di-$C_{1-4}$alkylamino, $C_{1-4}$alkanoylamino, $C_{1-4}$alkanoyl(N—$C_{1-4}$alkyl)amino, $C_{1-4}$alkanesulphonamido and $C_{1-4}$alkylS(O)$_n$- wherein n is zero, one or two.

'Alkyl' when used herein includes straight chain and branched chain substituents for example methyl, ethyl, n-propyl, isopropyl, n-butyl and isobutyl.

'Aryl' is used herein to describe optionally substituted, phenyl or naphthyl.

'Heteroaryl' is used herein to describe optionally substituted, preferably 5 or 6-membered mono- or 8–10 member bi-aromatic, groups having 1–4 ring heteroatoms, selected from nitrogen,. oxygen and sulphur. For example, pyridyl, pyrimidyl, pyrazinyl, pyridazinyl, thienyl, thiazolyl, oxazolyl, thiadiazolyl, imidazyl, pyrrolyl, isothiazolyl, quinolyl, isoquinolyl, quinoxalinyl, quinoxalinyl and cinnolinyl.

'$C_{3-10}$cycloalkyl' is used herein to describe optionally substituted, saturated carbocyclic ring systems. For example cyclopropyl, cyclobutyl, cyclopentyl and cyclohexyl.

'Heterocyclyl' is used herein to describe optionally substituted, saturated or partially saturated 5–6 membered mono or 8–10 membered bicyclic ring systems having 14 ring heteroatoms selected from nitrogen, oxygen and sulphur. For example piperidyl, pyrrolidinyl, piperazinyl, morpholinyl, pyrazolinyl, pyrroldinyl and imidazolinyl.

The term 'acylamino' includes compounds of the formula

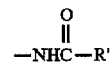

wherein R' is optionally substituted: $C_{1-6}$alkyl, phenyl, benzyl, heteroaryl, hetroarylC$_{1-4}$alkyl, or of the formula $R^{50}$—C(=N—OR$^{51}$)— wherein $R^{50}$ is phenyl or heteroaryl and $R^{51}$ is hydrogen or optionally substituted: $C_{1-6}$alkyl or benzyl.

In particular 'acylamino' is of the formula $R^{50}$—C(=N—OR$^{51}$)— wherein $R^{50}$ is 2-aminothiazol-4-yl, 5-amino-1,2,4-thiadiazol-3-yl or 2-aminooxazol-4-yl and $R^{51}$ is $C_{1-6}$alkyl or carboxyC$_{1-6}$alkyl.

Examples of substituents for aryl, heteroaryl, heterocyclyl and $C_{3-10}$cycloalkyl include, halo, nitro, cyano, $C_{1-4}$alkyl, carboxy, amino, hydroxy, $C_{1-4}$alkylamino, di-($C_{1-4}$alkyl)amino, $C_{1-4}$alkoxycarbonyl, sulpho, carbamoyl, $C_{1-4}$alkylcarbamoyl, di-($C_{1-4}$alkyl)carbamoyl, $C_{1-4}$alkanoyl, $C_{1-4}$alkoxy, $C_{1-4}$alkylthio, $C_{1-4}$alkylsulphinyl and $C_{1-4}$alkylsulphonyl.

The present invention covers all epimeric, diastereoisomeric and tautomeric forms of the compounds of the formula (I) wherein the absolute stereochemistry at the 7-position is as illustrated in formula (I). When a bond is represented by a wedge, this indicates that in three dimensions the bond would be coming out of the paper and when a bond is hatched, this indicates that in three dimensions the bond would be going back into the paper.

Particular compounds of the present invention are
(7R,8S)-5-acetoxy-8-(1-hydroxyethyl)-9-oxo-1-azabicyclo [5.2.0]non-2,4-diene-2-carboxylic acid;
(7R,8S)-8-((1R)-1-hydroxyethyl)-5-methylthio-9-oxo-1-azabicyclo[5.2.0]non-2,4-diene-2-carboxylic acid;
(7R,8S)-8-((1R)-1-hydroxyethyl)-5-methanesulphonyl-9-oxo-1-azabicyclo[5.2.0]non-2,4-diene-2-carboxylic acid;
(7R,8S)-5-(2-aminoethylthio)-8-((1R)-1-hydroxyethyl)-9-oxo-1-azabicyclo[5.2.0]-2,4-diene-2-carboxylic acid; or
(7R,8S)-5-(2-aminoethylsulphonyl)-8-((1R)-1-hydroxyethyl)-9-oxo-1-azabicyclo[5.2.0]-2,4-diene-2-carboxylic acid; or pharmaceutically acceptable salts thereof.

Suitable pharmaceutically acceptable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. For the avoidance of doubt there may be one or more salt-forming cations dependent on the number of carboxylic acid functions and the valency of said cations.

Preferred pharmaceutically acceptable salts are sodium and potassium salts. However, to facilitate isolation of the salt during preparation, salts which are less soluble in the chosen solvent may be preferred whether pharmaceutically acceptable or not.

In vivo hydrolysable esters are those pharmaceutically acceptable esters that hydrolyse in the human body to produce the parent compound. Such esters can be identified by administering, eg. intravenously to a test animal, the compound under test and subsequently examining the test animal's body fluids. Suitabe in vivo hydrolysable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy-$C_{1-6}$alkyl esters for example 1-cyclohexyloxycarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention. Suitable in vivo hydrolysable ester forming groups for hydroxy include acetyl, propionyl, pivaloyl, $C_{1-4}$alkoxycarbonyl for example ethoxycarbonyl and phenylacetyl.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known antibacterial drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids (for example see EP-A-178911) which reduce adverse effects on the kidney.

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

Composition 1
Compound of Example 1 50 mg
Compound 2
Compound of Example 1 50 mg
Glycine 31 mg The pharmaceutical compositions of the invention will normally be administered to man in order to combat infections caused by bacteria, in the same general manner as that employed for imipenem due allowance being made in terms of dose levels for the potency and duration of action of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily dose is 0.05 to 5 g of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (II):

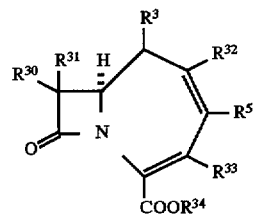

wherein $R^3$ and $R^5$ are as hereinabove defined; $R^{30}$ is $R^1$ or protected $R^1$; $R^{31}$ is $R^2$ or $R^{30}$ and $R^{31}$ together are optionally substituted $C_{1-6}$alkylene wherein any optional substituents are optionally protected; $R^{32}$ is $R^4$ or protected $R^4$; $R^{33}$ is $R^6$ or protected $R^6$; and —$COOR^{34}$ is carboxy or protected carboxy; and wherein at least one protecting group is present: and thereinafter if necessary;

(i) forming a pharmaceutically acceptable salt,
(ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minumum disturbance of groups elsewhere in the molecule.

The compounds of the formula II are novel and form another aspect of the invention.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1-20 carbon atoms).

Examples of carboxy protecting groups include straight or branched chain (1-12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2-6C)alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

Preferred methods for removal of the p-nitrobenzyl group is hydrogenation using a palladium catalyst or treatment with zinc powder in an aqueous acidic medium.

In another aspect of the present invention the compounds of the formula (I) and (II) may be prepared:

a) for compounds of the formula (I) wherein $R^4$ is of the formula —$SR^7$ or for compounds of the formula (II) wherein $R^{32}$ is of the formula —$SR^{7'}$ wherein $R^{7'}$ is $R^7$ or protected $R^7$, by reacting a compound of the formula $HSR^{7'}$ (compound B) with a compound of the formula (III)

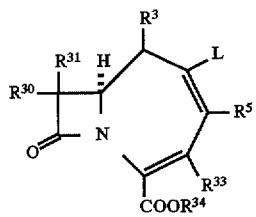

wherein $R^3$, $R^5$, $R^{30}$, $R^{31}$, $R^{33}$ and $R^{34}$ are as hereinabove defined and L is a leaving group;

b) for compounds of the formula (I) wherein $R^4$ is of the formula —$OR^{18}$ or for compounds of the formula (II) wherein $R^{32}$ is of the formula —$OR^{18'}$ wherein $R^{18'}$ is $R^{18}$ or protected $R^{18}$; by reacting a compound of the formula $HOR^{18'}$ (compound D) with a compound of the formula (III) wherein L, $R^3$, $R^5$, $R^{30}$, $R^{31}$, $R^{33}$ and $R^{34}$ are as hereinabove defined;

c) for compounds of the formula (I), wherein $R^4$ is of the formula —$N(R^{19})R^{20}$ or for compounds of the formula (II) wherein $R^{32}$ is of the formula —$N(R^{19'})R^{20'}$ wherein —$N(R^{19'})R^{20'}$ is —$N(R^{19})R^{20}$ or protected —$N(R^{19})R^{20}$:

(i) by reacting a compound of the formula $HN(R^{19'})R^{20'}$ (compound E) with a compound of the formula (III) wherein L, $R^3$, $R^5$, $R^{30}$, $R^{31}$, $R^{33}$ and $R^{34}$ are as hereinabove defined; or ii) converting a compound of the formula (IIIA):

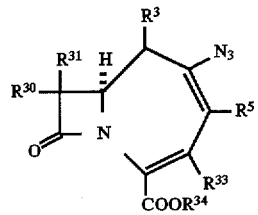

wherein $R^3$, $R^5$, $R^{30}$, $R^{31}$, $R^{33}$ and $R^{34}$ are as hereinbefore defined to a compound of the formula (I) or (II);

d) for compounds of the formula (I), wherein $R^4$ is optionally substituted $C_{1-10}$alkyl, optionally substituted aryl or of the formula —$CH_2R^{21}$ or compounds of the formula (II) wherein $R^{32}$ is optionally substituted $C_{1-10}$alkyl, optionally substituted aryl, protected substituted $C_{1-10}$alkyl, protected aryl or is of the formula —$CH_2R^{21'}$ wherein $R^{21'}$ is $R^{21}$ or protected $R^{21}$; by reacting a compound of the formula $R^{35}R^{36}R^{37}SnR^{38}$ (compound F) with a compound of the formula (III) wherein L, $R^3$, $R^5$, $R^{30}$, $R^{31}$, $R^{33}$ and $R^{34}$ are as hereinabove defined and $R^{35}$–$R^{37}$ are $C_{1-6}$alkyl and $R^{38}$ is optionally substituted $C_{1-10}$alkyl, aryl or of the formula —$CH_2R^{21'}$;

e) by cyclising a compound for the formula (IV):

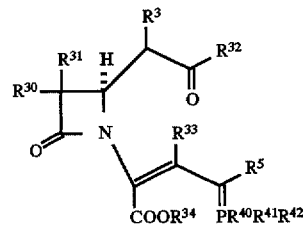

wherein $R^3$,$R^5$,$R^{30}$–$R^{34}$ are as hereinabove defined and $R^{40}$–$R^{42}$ are independently selected from $C_{1-6}$alkoxy, phenyl and phenoxy, wherein any phenyl group is optionally substituted with $C_{1-3}$alkyl or $C_{1-3}$alkoxy; and wherein any functional group is optionally protected and thereinafter if necessary:

(i) removing any protecting groups;
(ii) forming a pharmaceutically acceptable salt;
(iii) esterifying to form an in vivo hydrolysable ester.

Suitably, in the compound of the formula III, L is the reactive ester of a hydroxy group such as a sulphonate (for example $C_{1-6}$alkanesulphonyloxy, trifluoromethanesulphonyloxy, benzenesulphonyloxy, toluenesulphonyloxy) or a phosphoric ester (for example a diarylphosphoric ester such as diphenylphosphoric ester). Preferably L is trifluoromethanesulphonyloxy.

The reaction between compounds of the formula (III) and compounds B, D and E may be carried out under conditions known in the carbapenem art for the displacement of a leaving group in the carbapenem with a nucleophile. For example see EP-A-430037, WO 91/14687, EP-A405774 and U.S. Pat. No. 4,530,841. In general by reacting the compounds of the formulae (III) with compounds B, D or E in an inert organic solvent in the presence of a base. For example, the reaction between compounds of the formula (III) and B is conveniently performed in a temperature range of –40° C. to 50° C., in an inert organic solvent such as tetrahydrofuran, toluene, chloroform, ethyl acetate, N,N-dimethylformamide, acetonitrile or benzene, in the presence of a base such as a tertiary aliphatic amine.

The reaction between compounds of the formula (III) and compounds F is conveniently carried out in an aprotic polar solvent such as tetrahydrofuran, in the presence of a metal halide, such as zinc chloride, a palladium compound, such as $Pd_2(DBA).CHCl_3$, and a phosphine, such as tri(2,4,6-trimethoxyphenyl)phosphine. For example, in carbapenem art, see EP-A-444889.

The conversion of compound (IIIA) to a compound of the formula (I) or (II) may be carried out under conditions known in the carbapenem art for the conversion of an azide to an amine. For example see U.S. Pat. No. 4,310,538.

The compounds of the formulae (III), (IIIA) and (IV) are novel and form other aspects of the invention.

The compounds of the formula (IIIA) may be prepared by reacting a compound of the formula (III) with a source of azide, for example $HN_3$ or $NaN_3$.

The compounds of the formula (III) may be prepared from a compound of the formula (V):

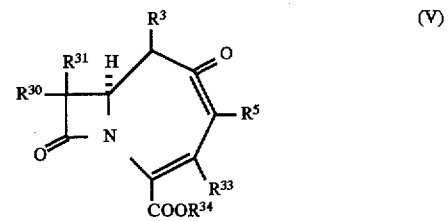

wherein $R^3, R^5, R^{30}, R^{31}, R^{33}$ and $R^{34}$ are as hereinabove defined. For example when L is a sulphonate or phosphoric ester, by reacting compounds of the formula (V) with a reactive derivative of L. Suitable reactive derivatives include, for example, an acid anydride such as methane, sulphonic anhydride, trifluoromethanesulphonic anhydride, p-toluenesulphonic anhydride, an acid chloride such as methanesulphonyl chloride, p-toluenesulphonyl chloride or diphenylchlorophosphate.

The reaction is conveniently carried out in an inert solvent, such as methylene chloride, tetrahydrofuran or acetonitrile, in the presence of a base, such as a tertiary aliphatic amine, for example triethylamine, in a temperature range of –78° C. to 30° C.

The compound of the formula (V) may be prepared as outlined in Scheme I.

Scheme I

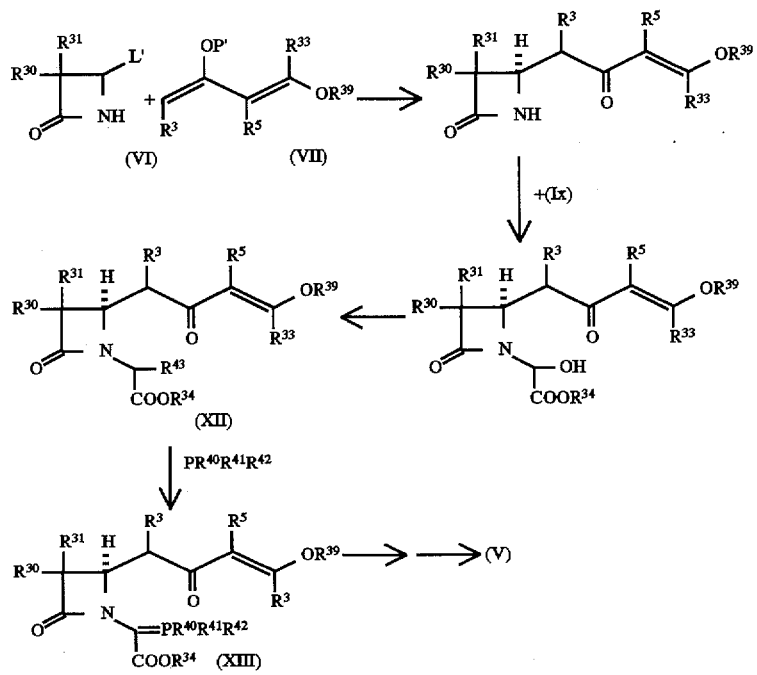

wherein compounds of the formulae (IX) are either of the formula $R^{34}OC(O)CHO$ or $R^{34}OC(O)CH(OH)_2$ and $R^3, R^5, R^{30}, R^{31}, R^{33}, R^{34}$ and $R^{40}-R^{42}$ are as hereinabove defined and $R^{39}$ is $C_{1-6}$alkyl, $R^{43}$ is a halogen atom, $L^1$ is a leaving group, $p^1$ is a protecting group and (XI) is a halogenating agent.

The reaction between compounds of the formulae (VI) and (VII) may be carried out in an organic solvent such as dichloromethane, tetrahydrofuran, ether, dioxane or acetone in a temperature range of $-100°$ C. to $50°$ C. A suitable protecting group ($P^1$) is a silyl protecting group, for example trimethylsilyl. A suitable leaving group is, for example, acetoxy.

The reaction between the compounds of the formulae (VIII) and (IX) is conveniently carried out in a solvent such as acetonitrile, tetrahydrofuran, dioxane or acetone at an elevated temperature, for example $40°$ C. to $100°$ C., in the presence of a base, such as triethylamine.

Suitable halogenating agents in the conversion of a compound of the formula (X) to a compound of the formula (XII) include N-bromosuccinimide and sulphonylchloride. Suitable conditions are known in the art, for example using an inert organic solvent such as THF, in a temperature range of $-30°$ C. to ambient temperature. Compound (XII) may be isolated or converted to the ylide in situ.

The reaction between the compounds of the formula $PR^{40}R^{41}R^{42}$ and (XII) is normally carried out in an inert solvent such as acetonitrile, dichloromethane, ethyl ether, tetrahydrofuran or toluene, in a temperature range of $20°$ C. to reflux. The resulting phosphonium compound may be isolated or deprotonated in situ to form a compound of the formula (XIII).

The $-C(R^5)=CR^{33}(OR^{39})$ group in the compounds of the formula (XIII) is a masked aldehyde or ketone which is hydrolysed to an aldehyde or ketone with, for example, paratoluene sulphonic acid monohydrate. Cyclisation of the aldehyde or ketone compound in situ forms a compound of the formula (V). The reaction is conveniently carried out in an inert solvent such as benzene, toluene or xylene in a temperature range of $80°$ C. to $150°$ C.

Compounds of the formula (IV) may be cyclised under similar conditions to that described for the cyclisation of a compound of the formula (XIII) for example in the presence of paratoluene sulphonic acid monohydrate.

The compounds of the formula (IV) may be prepared from compounds of the formula (XIV):

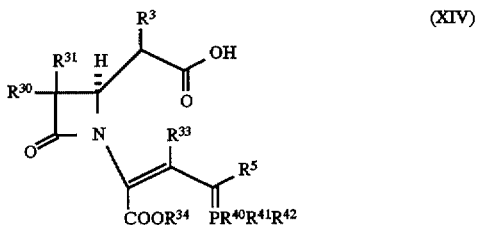

(XIV)

wherein $R^3, R^5, R^{30}, R^{31}, R^{33}, R^{34}$ and $R^{40}-R^{42}$ are as hereinabove defined.

For example, when $R^{32}$ is linked via a carbon atom, the compounds of the formula (XIV) wherein $R^{34}$ is a protecting group, can be converted to compounds of the formula (IV) by reacting with an activated acylating agent such as 2-pyridyl chlorothioformate and reacting this activated intermediate with a suitable Grignard reagent, such as $BrMgR^{32}$ under standard conditions known in the art. For example, in an inert solvent such as tetrahydrofuran or ether at $0°$ C.

Further examples are described for related reactions in U.S. Pat. No. 4,260,627, U.S. Pat. No. 4,543,257, Tetrahedron, 39, 2531 (1983) and J. Med. Chem. 30, 871 (1987).

The compounds of the formula (XIV) may be prepared as outlined in Scheme II.

Scheme II

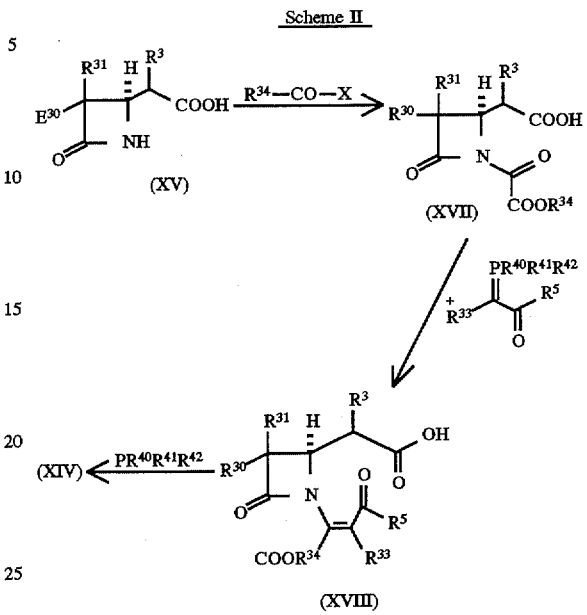

wherein $R^3, R^5, R^{30}, R^{31}, R^{33}, R^{34}$ and $R^{40}-R^{42}$ are as hereinabove defined and X is halo.

The reaction between compounds of the formulae (XV) and $R^{34}$—CO—X is conveniently carried out in an inert solvent such as tetrahydrofuran, ethyl acetate or dichloromethane in a temperature range of $0°$ C. to $40°$ C.

Preferably X is chlorine.

The reaction between compounds of the formulae (XVI) and (XVII) may be carried out under conditions known in the art for Wittig reactions. For example, the conditions described for the cyclisation of the compounds of the formula (VI).

The reaction between the compounds of the formulae $PR^{40}R^{41}R^{42}$ and (XVIII) is conveniently performed under conditions known in the art, for example, in an organic solvent such as toluene, xylene, ethyl acetate, chloroform, dichloromethane, acetonitrile or dimethylformamide. Typically the reaction is carried out at an elevated temperature for example $60°-150°$ C.

For examples of suitable conditions see EP-A-394991. The following biological test methods, data and Example serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and have a particularly good elimination half life in mammals. In general compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| Organism | MIC (μg/ml) Example | |
|---|---|---|
| | 1 | 3 |
| Strep. Pneumoniae | 8 | — |
| E. coli DC2 | 16 | 4 |

In the examples:

(a) THF means tetrahydrofuran; and (b) Evaporation of solvents was carried out under reduced pressure.

EXAMPLE 1

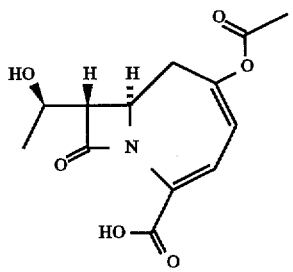

Method A (7R,8S)-5-Acetoxy-8-(1-hydroxyethyl)-9-oxo-1-azabicyclo [5.2.0]non-2,4-diene-2-carboxylic acid.

4-Methoxybenzyl (7R,8S)-5-acetoxy-8-[(1R)-1-hydroxyethyl]-9-oxo-1-azabicyclo[5.2.0]non-2,4-diene-2-carboxylate (29 mg, 0.07 mM) was dissolved in dichloromethane (3 ml) and cooled to −78° C. AlCl$_3$ (6 mg, 0.04 mM) was added and reaction took place instantaneously. Phosphate buffer (3 ml, PH7) was added and the mixture allowed to warm to ambient temperature. The aqueous phase was isolated, the solvent removed and the residue purified by subjecting to chromatography on HP20SS resin (10 ml), eluting with water. The appropriate fractions were lyophilised to give (7R,8S)-5-acetoxy-8-[(1R)-hydroxyethyl]-9-oxo-1-azabicyclo[5.2.0]non-2,4-diene-2-carboxylic acid (11 mg, 50%). Ms (-ve FAB) 280 (M−H)$^+$ Nmr: (90 MHz, D$_2$O): δ 1.46 (d, 3H); 2.37 (s, 3H); 3.07–3.21 (m, 3H); 3.87 (m, 1H); 5.89 (d, 1H); 6.02 (d, 1H).

The starting material was prepared as follows:

(3R,4R) 4-acetoxy-3-[(1R)-(1-(tert-butyldimethylsilyloxy)ethyl)]azetidin-2-one (2 g, 56.96 mM) was dissolved in dichloromethane (150 ml) at ambient temperature and 4-methoxy-2-trimethylsilyloxybut-1,3-diene (1.5 ml, 7.65 mM) added followed by zinc iodide (2.2 g, 17 mM). The reaction mixture was shielded from light and stirred for 15 hours. The mixture was then washed with a 5% aqueous solution of sodium bicarbonate (30 ml) and then water (30 ml). The organic phase was dried with magnesium sulphate and the solvent evaporated. The residue was purified by chromatography on silica, eluting with ethyl acetate/ dichloromethane (1:1) to give (3S,4R) 3-((1R)-1-(tert-butyldimethylsilyloxy)ethyl)-4-(4-methoxy-2-oxobut-3-en-1-yl)azetidin-2-one (0.96 g, 43%).

Nmr: (90 MHz, CDCl$_3$): δ 0.07 (s, 7H); 0.87 (s, 9H); 1.22 (d, 3H); 2.45–3.10 (m, 3H); 3.73 (s, 3H); 3.90–4.30 (m, 2H); 5.57 (d, 1H); 6.05 (brs, 1H); 7.60 (d, 1H).

A mixture of (3S ,4R) 3-((1R)-1-(tert-butyldimethylsilyloxy)ethyl)-4-(4-methoxy-2-oxobut-3-en-1-yl)azetidin-2-one (100 mg, 0.3 mM), 4-methoxybenzyl dihydroxyacetate (72 mg, 0.33 mM) and 2 drops of triethylamine in benzene (5 ml) was heated at reflux for 1 hour. The solvent was evaporated and the product purified by subjecting to chromatography on silica, eluting with ether to give 4-methoxybenzyl 2-[(3S,4R)-3-[(1R)-1-(tert-butyldimethylsilyloxy)-ethyl]-4-[4-methoxy-2-oxobut-3-en-1-yl]-2-azetidinone-1-yl]-2-hydroxy-acetate (147 mg, 93%). IR (film, NaCl) 3310, 1745.

4-Methoxybenzyl 2-[(3S,4R)-3-[(1R)-1-(tert-butyl-dimethylsilyloxy)ethyl]-4-[4-methoxy-2-oxobut-3-en-1-yl]-2-azetidinone-1-yl]-2-hydroxyacetate (4.16 g, 8 mM) was dissolved in THF (150 ml) and cooled to −20° C. 2,6-Lutidine (3 ml, 24 mM) was added, then thionyl chloride (0.9 ml, 12 mM). The mixture was allowed to warm to ambient temperature over 30 minutes. The mixture was filtered, the solvent evaporated, the residue redissolved in benzene, filtered and the solvent evaporated. The residue was redissolved in THF (150 ml) and triphenylphosphine (4.2 g, 16 mM), 2,6-lutidine (2 ml, 16 mM) and sodium iodide (0.25 g, 1.6 mM) added successively. The mixture was stirred for 15 hours at ambient temperature, after which it was filtered, evaporated and purified by subjecting to chromatography on silica, eluting with ethyl acetate/ cyclohexane (1:1) to give 4-methoxybenzyl 2-[(3S,4R)-3-[ (1R)-1-(tertbutyldimethylsilyloxy)ethyl]-4-[4-methoxy-2-oxobut-3-en-1-yl]-2-azetidinon-1-yl]-2-(triphenylphosphoronylidene)acetate (4.25 g, 66.4%). IR (film, NaCl) 3450, 1730

Toluenesulphonic acid (4 mg, 0.03 mM) was added to 4-methoxybenzyl 2-[(3S,4R)-3-[(1R)-1-(tertbutyldimethylsilyloxy)ethyl]-4-[4-methoxy-2-oxobut-3-en-1-yl]-2-azetidinon-1-yl]-2-(triphenylphosphoronylidene)acetate (240 mg, 0.3 mM) in toluene (10 ml) and the mixture warmed to 50° C. After 3 hours, the mixture was diluted with ethyl acetate (40 ml) and washed with a 5% aqueous solution of sodium bicarbonate (20 ml). The organic phase was dried with magnesium sulphate, the solvent evaporated and the residue purified by subjecting to chromatography on a silica column (20 ml), eluting with ethyl acetate/dichloromethane to give 4-methoxybenzyl (7R,8S)-8-[(1R)-1-(tert-butyldimethylsilyloxy)ethyl]-5,9-dioxo-1-azabicyclo[5.2.0] non-2-ene-2-carboxylate (105 mg, 76.6%).

Nmr: (90 MHz, CDCl$_3$): δ 0.05 (s, 3H); 0.07 (s, 3H); 0.86 (s, 9H); 1.26 (d, 3H); 2.65–3.00 (m, 3H); 3.35 (dd, 2H); 3.80 (s, 3H); 3.90–4.35 (m, 2H); 5.18 (brs, 2H); 6.10 (t, 1H); 6.80–6.95 (m, 2H); 7.23–7.40 (m, 2H).

Triethylamine (77 μl, 0.55 mM) followed by acetyl chloride (23 μl, 0.3 mM) were added to a solution of 4-methoxybenzyl (7R,8S)-8-[(1R)-1-(tert-butyldimethylsilyloxy)-ethyl]-5,9-dioxo-1-azabicyclo[5.2.0]non-2-ene-2-carboxylate (120 mg, 0.25 mM) in dichloromethane (15 ml) cooled with an ice bath. The reaction occurred immediately. The solvent was evaporated and the residue purified by chromatography on a silica column, eluting with ethyl acetate/cyclohexane (1:3) to give 4-methoxybenzyl (7R,8S)-5-acetoxy-8-[(1R)-1-ter(t-butyldimethylsilyloxy)ethyl]-9-oxo-1-azabicyclo[5.2.0]non-2,4-diene-2-carboxylate (100 mg, 78%).

Nmr: (300 MHz, CDCl$_3$): δ 0.06 (s, 3H); 0.07 (s, 3H); 0.85 (s, 9H); 1.28 (d, 3H); 2.15 (s, 3H); 2.77 (dd, 1H); 2.84–2.87 (m, 2H); 3.67 (m, 1H); 3.80 (s, 3H); 4.30 (m, 1H); 5.21 (s, 2H); 5.75 (d, 1H); 6.08 (d, 1H); 6.88 (d, 2H); 7.35 (d, 2H). $^{13}$C (300 MHz, CDCl$_3$): δ −4.99, −4.47, −0.09, 17.76, 20.73, 22.72, 25.63, 40.43, 47.99, 55.16, 65.86, 67.24, 112.11, 113.03, 113.29, 127.66, 128.21, 130.35, 153.15, 159.63, 162.24, 163.54, 169.01.

To a solution of 4-methoxybenzyl (7R,8S)-5-acetoxy-8-[(1R)-1-(tert-butyldimethylsilyloxy)ethyl]-9-oxo-1-azabicyclo[5.2.0]non-2,4-diene-2-carboxylate (88 mg, 0.17 mM) in methanol (6 ml) was added hydrochloric acid (10 drops, 2N). After 6 hours the solvent was evaporated and the product purified by chromatography on silica (10 ml), eluting with ethyl acetate/dichloromethane, (1:1) to give 4-methoxybenzyl (7R,8S)-5-acetoxy-8-[(1R)-1-hydroxyethyl]-9-oxo-1-azabicyclo[5.2.0]non-2,4-diene-2-carboxylate (29 mg, 39%).

Nmr: (90 MHz, CDCl$_3$): δ 1.32 (d, 3H); 2.14 (s, 3H); 2.80–2.97 (m, 3H); 3.70 (m, 1H); 3.79 (s, 3H); 4.33 (m, 1H); 5.18 (s, 2H); 5.74 (d, 1H); 6.13 (d, 1H); 6.87 (d, 2H); 7.32 (d, 2H). MS (+ve FAB) 402 (M+H)$^+$

Method B

4-Nitrobenzyl(7R,8S)-5acetoxy-8-[(1R)-1-hydroxyethyl]-9-oxo-1-azabicyclo[5.2.0]non-2,4-diene-2-carboxylate (150 mg, 0.36 mmol) was dissolved in a 1:1 (v/v) mixture of THF and water (25 ml) at ambient temperature. The pH of the solution was adjusted with a pHstat to 3.6 and zinc powder (285 mg, 4.3 mmol) was added portion wise to the solution while the pH of the solution was maintained at 3.6 with 2N HCl. After 15 min, the pH was adjusted to 6.5, the suspension filtered over Celite and the THF evaporated in vacuo. The remaining aqueous solution was purified by column chromatography on a reverse phase silica gel (Nucleosil C18 10µ, 3.5×20 cm) with water as eluant. Lyophilisation of the appropriate fractions yielded (7R,8S)-5 Acetoxy-8-[(1R)-1-hydroxyethyl]-9-oxo-1-azabicyclo[5.2.0]non-2,4-diene-2-carboxylic acid, sodium salt (61 mg, 56%).

1H NMR (400 MHz, D2O) δ:1.31 (d, 3H); 2.22 (s, 3H); 2.94–2.96 (m, 2H); 3.01 (dd, 1H); 3.77 (m, 1H); 4.36 (m, 1H); 5.77 (d, 1H); 5.84 (d, 1H).

MS (ESI): 303 (MNa)+

The starting material was prepared as follows:

A mixture of (3S,4R) 3-[(1R)-1-(tert-butyldimethyl-silyloxy)ethyl]-4-[(4Z)-methoxy-2-oxobut-3-en-1-yl]-2-azetidinone (10 g, 30 mmol), 4-nitrobenzyl-1,1-dihydroxyacetate (7.2 g, 34 mmol) and triethylamine (1.6 ml, 11 mmol) in toluene (500 ml) was heated at reflux in a Dean-Stark apparatus in the presence of molecular sieves (4A°) for 6 hours. Additional 4-nitrobenzyl-1,1-dihydroxyacetate (1.5 g, 7 mmol) was added during the reaction. The solvent was evaporated and the residue purified by flash chromatography on silica using acetonitrile/dichloromethane (1:9) as eluant to give 4-nitrobenzyl 2-[(3S,4R)-3-[(1R)-1-(tert-butyldimethylsilyloxy)ethyl]4-[(4Z)-methoxy-2-oxobut-3-en-1-yl]-2-azetidinon-1-yl]-2-hydroxyacetate as two diastereoisomers (8.5 g, 53%).

*Less polar diastereoisomer:
1H NMR (400 MHz, CDCl3) δ:0.04(s, 3H); 0.06 (s, 3H); 0.85 (s, 9H); 1.21 (d, 3H); 2.81–2.96 (m, 3H); 3.70 (s, 3H); 4.15–4.21 (m, 2H); 5.18 (d, 1H); 5.23 (d, 1H); 5.44 (d, 1H); 5.46 (d, 1H); 5.59 (d, 1H); 7.53 (d, 2H); 8.21 (d, 2H).

*More polar diastereoisomer:
1H NMR (400 MHz, CDCl3) δ:0.03 (s, 6H); 0.83 (s, 9H); 1.24 (d, 3H); 2.82 (dd, 1H); 2.84 (d, 1H); 3.0 (dd, 1H); 3.75 (s, 3H); 4.06–4.10 (m, 2H); 4.74 (d, 1H); 5.33 (d, 1H); 5.38 (d, 1H); 5.58 (d, 1H); 5.60 (d, 1H); 7.58 (d, 2H); 7.62 (d, 1H); 8.23 (d, 2H).

To a solution of 4-nitrobenzyl 2-[(3S,4R)-3-[(1R)-1(tert-butyldimethylsilyloxy)-ethyl]-4-[(4Z)-methoxy-2-oxobut-3-en-1-yl]-2-azetidinon-1-yl]-2-hydroxyacetate (8.49 g, 15.8 mmol) in THF (300 ml) at −20° C. was added successively 2,6-lutidine (5.5 ml, 47.5 mmol) and thionylchloride (1.7 ml, 24 mmol). The cooling bath was removed and the reaction mixture stirred at ambient temperature for 30 minutes. The mixture was filtered, the solvent evaporated, the residue redissolved in toluene, the solution again filtered and evaporated. The residue was taken up in THF (300 ml) and triphenylphosphine (8.3 g, 32 mmol), 2,6-lutidine (3.7 ml, 32 mmol) and sodium iodide (0.5 g, 32 mmol) were added successively. The reaction mixture was stirred at ambient temperature for 1 hour, filtered and evaporated. The residue was purified by flash chromatography on silica using dichloromethane/ethyl acetate (8:2) as eluant to afford the title compound 4-nitrobenzyl 2-[(3S,4R)-3[(1R)-1-(tert-butyldimethylsilyloxy)ethyl]-4-[(4Z)-methoxy-2-oxobut-3-en-1-yl]-2-azetidinon-1-yl]-2-(triphenylphosphoranylidene) acetate (7.5 g, 58% ).

1H NMR (400 MHz, CDCl3) δ:−0.13 (s, 2H); −0.06 (s, 3H); 0.76 (s, 9H); 1.10 (d, 3H); 2.52–2.67 (m, 2H); 2.88–3.09 (m, 2H); 3.18–3.40 (m, 1H); 3.65 (s, 3H); 4.72–5.76 (complex pattern, 3H); 6.68 (d, 1H); 7.43–8.25 (m, 19 H).

A solution of 4-nitrobenzyl 2-[(3S,4R)-3-[(1R)-1(tert-butyldimethyl-silyloxy)ethyl]-4-[(4Z)-methoxy-2-oxobut-3-en-1-yl]-2-azetidinon-1-yl]-2-(triphenyl-phosphoranylidene)acetate (6.9 g, 8.4 mmol) and para toluenesulphonic acid monohydrate (0.56 g, 2.9 mmol) in toluene (280 ml) was heated at 80° C. for 10 minutes and then stirred at 60° C. for 5 hours. Additional para toluenesulphonic acid monohydrate (0.51 g, 2.7 mmol) was added during the reaction.

The solvent was removed under reduced pressure, the residue was taken up in ethyl acetate, washed with a 5% aqueous solution of NaHCO3 and water. The organic phase was dried over magnesium sulphate, the solvent evaporated and the residue purified by flash chromatography on a silica gel column, eluting with dichloromethane/ethyl acetate (85:15) to afford 4-nitrobenzyl (7R,8S)-8-[(1R)-1-(tert-butyldimethylsilyloxy)ethyl]-5,9-dioxo-1-azabicyclo[5.2.0] non-2-ene-2-carboxylate (1.67 g, 41%).

1H NMR (400 MHz, CDCl3) δ:0.04 (s, 3H); 0.07 (s, 3H); 0.85 (s, 9H); 1.26 (d, 3H); 2.93–3.01 (m, 3H); 3.41 (ddd, 1H); 4.06 (m, 1H); 4.21 (m, 1H); 5.30 (d, 1H); 5.37 (d, 1H); 6.18 (dd, 1H); 7.57 (d, 2H); 8.22 (d, 2H).

MS (ESI): 511 (MNa+).

Triethylamine (1.1 ml, 7.5 mmol) followed by acetyl chloride (0.295 ml, 4.1 mmol) were added to a solution of 4-nitrobenzyl (7R,8S)-8-[(1R)-1-(tertbutyldimethylsilyloxy)-ethyl]-5,9-dioxo-1-azabicyclo [5.2.0]non-2-ene-2-carboxylate (1.67 g, 3.4 mmol) in anhydrous dichloromethane (220 ml) cooled with an ice bath. After 5 minutes, the reaction mixture was washed with water and dried over magnesium sulphate. The solvent was evaporated and the residue purified by flash chromatography, eluting with dichloromethane/ethyl acetate (95:5) to give 4-nitrobenzyl (7R,8S)-5-acetoxy-8-[(1R)-1-(tertbutyldimethyl-silyloxy)ethyl]-9-oxo-1-azabicyclo [5.2.0]non-2,4-diene-2-carboxylate (1.4 g, 77%).

1H NMR (400 MHz, CDCl3) δ:0.04 (s, 3H); 0.07 (s, 3H); 0.85 (s, 9H); 1.26 (d, 3H); 2.93–3.01 (m, 3H); 3.37 (dd, 1H); 3.45 (dd, 1H); 4.06 (m, 1H); 4.21 (m, 1H); 5.31 (d, 1H); 5.37 (d, 1H); 6.18 (dd, 1H); 7.57 (d, 2H); 8.22 (dd, 2H).

To a solution of 4-nitrobenzyl (7R,8S)-5-acetoxy-8-[(1R)-1-(tert-butyldimethylsilyloxy)ethyl]-9-oxo-1-azabicyclo [5.2.0]non-2,4-diene-2-carboxylate (1.35 g, 2.5 mmol) in anhydrous THF (75 ml) was added under argon successively acetic acid (2.18 ml, 38 mmol) and a 1.1M THF solution of N-tetrabutylammonium fluoride (12 ml, 12.7 mmol). The reaction mixture was stirred at ambient temperature for 3 days. Additional acetic acid (0.44 ml, 7.6 mmol) and N-tetrabutylammonium fluoride (2.4 ml, 25 mmol) were added after 2 days. THF was evaporated, the residue taken up in ethyl acetate and the solution was successively washed with a 5% aqueous solution of NaHCO3 and water. The organic phase was dried over magnesium sulphate, the solvent evaporated and the residue purified by flash chromatography on a silica gel column, eluting with dichloromethane/ethyl acetate (1:1) to afford 4- nitrobenzyl (7R,8S)-5 acetoxy-8-[(1R)-hydroxethyl]-9-oxo-1-azabicyclo[5.2.0]non-2,4-diene-2-carboxylate as a foam (0.5 g, 47%).

1H NMR (400 MHz, CDCl3) δ:1.36 (d, 3H); 2.18 (s, 3H); 2.86 (dd, 1H); 2.92–2.94 (m, 2H); 3.72 (m, 1H); 4.35 (m, 1H); 5.35 (s, 2H); 5.82 (dd, 1H); 6.22 (d, 1H); 7.59 (d, 2H); 8.23 (d, 2H).

MS (ESI): 439 (MNa)+

EXAMPLE 2

(7R,8S)-8-[(1R)-1-Hydroxyethyl]-5-methylthio-9-oxo-1-azabicyclo[5.2.0]non-2,4-diene-2-carboxylic acid, sodium salt

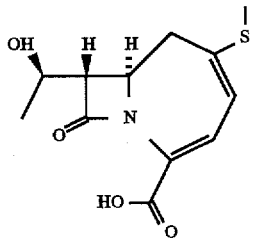

To a solution of 4-nitrobenzyl (7R,8S)-8-[(1R)-1-hydroxyethyl]-5-methylthio-9-oxo-1-azabicyclo [5.2.0]non-2,4-diene-2-carboxylate (179 mg, 0.44 mmol) in DMF (45 ml) was added 10% palladium on charcoal (80 mg). The reaction mixture was stirred under a hydrogen atmosphere for 1.5 hours. The catalyst was filtered off, the organic phase partially concentrated and purified by chromatography on HP20SS resin (60 ml) with a gradient of CH3CN (0 to 50%) in water as mobile phase. Freeze drying of the appropriate fractions gave the expected acid (80 mg) only partially purified. The solid was suspended in water (6 ml) and solubilisised by adjusting the pH of the solution to 7.3 with an aqueous saturated solution of NaHCO3. The mixture was then purified by reverse phase chromatography (Nucleosil C18 10μ, 3.5×20 cm) with water as eluant to give, after freeze drying, the title compound (36 mg, 32% yield) as a yellow solid.

1H NMR (400 MHz, D2O) δ:1.32 (d, 3H); 2.34 (s, 3H); 2.82 (ddd, 1H); 2.94 (d, 1H); 2.99 (dd, 1H); 3.72 (ddd, 1H); 4.35 (m, 1H); 5.66 (brd, 1H); 5.96 (d, 1H).

MS (FAB+ve): 292 (MNa)+

The starting materials were prepared as follows:

To a solution of 4-nitrobenzyl (7R,8S)-8-[(1R)-1-(tert-butyldimethylsilyloxy)ethyl]-5,9-dioxo-1-azabicyclo[5.2.0] non-2-ene-2-carboxylate (1.5 g, 3.07 mmol) in acetonitrile (15 ml) was added at 0° C. N,N-diisopropylethylamine (1.1 ml, 6.45 mmol). The reaction mixture was cooled at −40° C. and trifluoromethanesulfonic anhydride (0.57 ml; 3.38 mmol) was added. After 5 minutes, further N,N-diisopropylethylamine (1.1 ml, 6.45 mmol) was added to the reaction mixture. Methylmercaptan was then bubbled through the solution at −40° C. during a few seconds. The mixture was allowed to warm to ambient temperature over 1.5 hours. The solvent was evaporated and the residue purified by chromatography on silica gel eluting with ethyl acetate/dichloromethane 3:97 to give 4-nitrobenzyl (7R,8S) -8-[(1R)-1-(tert-butyldimethylsilyloxy)ethyl]5-methylthio-9-oxo-1-azabicyclo[5.2.0]non-2,4-diene-2-carboxylate (776 mg, 47%).

1H NMR (CDCl3) δ:0.03 (s, 3H); 0.07 (s, 3H); 0.84 (s, 9H); 1.28 (d, 3H); 2.32 (s, 3H); 2.69 (ddd, 1H); 2.78 (dd, 1H); 2.87 (d, 1H); 3.61 (brd, 1H); 4.29 (m, 1H); 5.30 (d, 1H); 5.38 (d, 1H); 5.52 (brd, 1H); 6.29 (d, 1H); 7.60 (d, 2H); 8.21 (d, 2H).

MS (ESI):541 (MNa)+.

To a solution of 4-nitrobenzyl (7R,8S)-8-[(1R)-1-(tert-butyldimethylsilyloxy)ethyl]-5-methylthio-9-oxo-1-azabicyclo [5.2.0]non-2,4-diene-2-carboxylate (213 mg, 0.41 mmol) in anhydride THF (8 ml) was added acetic acid (0.35 ml) and a 1.1M solution in tetrahydrofuran of tetrabutylammonium fluoride (1.9 ml; 2.04 mmol). After stirring for 3 days at ambient temperature, the reaction mixture was diluted with ethyl acetate (20 ml) and then washed with an 5% aqueous solution of NaHCO3 and water. After evaporation of the solvents, the residue was taken up with methylene chloride. The insoluble material was filtered off and identified as 4-nitrobenzyl (7R,8S)-8-[(1R)-1-hydroxyethyl] -5-methylthio-9-oxo-1-azabicyclo[5.2.0]non-2,4-diene-2-carboxylate: The filtrate was concentrated and the residue was purified by chromatography on silica gel eluting with ethyl acetate/dichloromethane 3:7 to give an other batch of the 4-nitrobenzyl (7R,8S)-8-[(1R)-1-hydroxyethyl]-5-methylthio-9-oxo-1-azabicyclo-[5.2.0]non-2,4-diene-2-carboxylate (total=102 mg, 62% overall yield).

1H NMR (400 MHz, CDCl3) δ:1.37 (d, 3H); 1.87 (d, 1H); 2.33 (s, 3H); 2.74 (ddd, 1H); 2.85 (dd, 1H); 2.93 (d, 1H); 3.64 (dt, 1H); 4.34 (m, 1H); 5.32 (d, 1H); 5.37 (d, 1H); 5.54 (brd, 1H); 6.35 (d, 1H); 7.60 (d, 2H); 8.22 (d, 2H).

MS (ESI): 427 (MNa)+.

EXAMPLE 3

(7R, 8S)-8-[(1R)-1-Hydroxyethyl]-5-methanesulphonyl-9-oxo-1-azabicyclo [5.2.0]non-2,4-diene-2-carboxylic acid, sodium salt

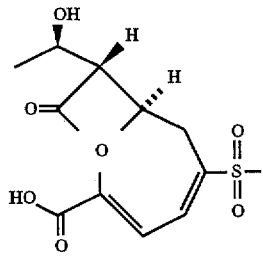

The title compound was prepared from 4-nitrobenzyl (7R,8S)-8-[(1R)-1-hydroxyethyl]-5-methanesulphonyl-9-oxo-1-azabicyclo [5.2.0]non-2,4-diene-2-carboxylate by the procedure described in Example 1, method B.

1H NMR (400 MHz, D2O) δ:1.34 (d, 3H); 2.90 (ddd, 1H); 3.15 (s, 3H); 3.27 (dd, 1H); 3.49 (d, 1H); 3.82 (m, 1H); 4.38 (m, 1H); 5.78 (d, 1H); 7.10 (dd, 1H).

MS (ESI): 346 (MNa)+

The starting materials were prepared as follows:

3-Chloroperoxybenzoic acid at (50% pure, 0.89 g, 2.58 mmol) was added at 0° C. to a solution of 4-nitrobenzyl (7R,8S)-8-[(1R)-1-(tert-butyldimethylsilyloxy)ethyl]-5-methylthio-9-oxo-1-azabicyclo[5.2.0]non-2,4-diene-2-carboxylate (0.67 g, 1.29 mmol) in dichloromethane (17 ml). The reaction mixture was stirred at 0° C. for 3 hours. The solution was washed with an 5% aqueous solution of NaHCO3, water and dried over magnesium sulphate. The solvent was evaporated and the residue purified by flash chromatography, eluting with dichloromethane/ethyl acetate (85:15) to give 4-nitrobenzyl (7R,8S)-8-[(1R)-1-(tert-butyldimethylsilyloxy)ethyl]-5-methanesulphonyl-9-oxo-1-azabicyclo[5.2.0]non-2,4-diene-2-carboxylate (0.48 g, 67%).

1H NMR (400 MHz, CDCl3) δ:0.02 (s, 3H); 0.08 (s, 3H); 0.83 (s, 9H); 1.28 (d, 3H); 2.64 (ddd, 1H); 2.94 (s, 3H); 2.99 (dd, 1H); 3.56 (d, 1H); 3.73 (m, 1H); 4.34 (m, 1H); 5.38 (s, 2H); 6.14 (d, 1H); 7.14 (dd, 1H); 7.59 (d, 2H); 8.23 (d, 2H).

MS (ESI): 573 (MNa)+

4-Nitrobenzyl (7R,8S)-8-[(1R)-1-hydroxyethyl]-5-methanesulphonyl-9-oxo-1-azabicyclo [5.2.0]non-2,4-diene-2-carboxylate was prepared from 4-nitrobenzyl (7R, 8S)-8-[(1R)-1-(tert-butyldimethylsilyloxy)ethyl]-5-methanesulphonyl-9-oxo-1-azabicyclo [5.2.0]non-2,4-diene-2-carboxylate by a similar procedure to that described in Example 1, method B.

1H NMR (400 MHz, CDCl3): δ:1.38 (d, 3H); 2.00 (d, 1H); 2.69 (ddd, 1H); 2.95 (s, 3H); 3.04 (dd, 1H); 3.62 (dd, 1H); 3.73 (m, 1H); 4.38 (m, 1H); 5.38 (s, 2H); 6.22 (d, 1H); 7.16 (dd, 1H); 7.59 (d, 2H); 8.23 (d, 2H).

MS (ESI): 459 (MNa)+; 436 (MH)+.

EXAMPLE 4

(7R,8S)-5-(2-Aminoethylthio)-8-[(1R)-1-hydroxyethyl]-9-oxo-1-azabicyclo [5.2.0]non-2,4-diene-2-carboxylic acid

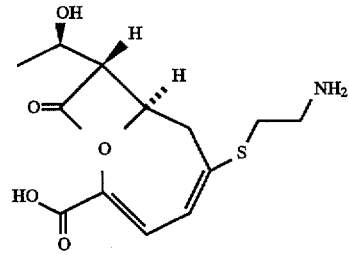

The title compound was prepared from 4-nitrobenzyl (7R,8S)-8-[(1R)-1-hydroxyethyl]-5-[2-(4-nitrobenzyloxycarbonyl)-aminoethylthio-9-oxo-1-azabicyclo [5.2.0]non-2,4-diene-2-carboxylate by a similar procedure to that described in Example 1, method B.

1H NMR (400 MHz, D2O): δ:1.32 (d, 3H); 2.83 (ddd, 1H); 3.00–3.05 (m, 2H); 3.08–3.20 (m, 2H); 3.22–3.31 (m, 2H); 3.72 (m, 1H); 4.35 (m, 1H); 5.86 (d, 1H); 5.98 (m, 1H).

MS (ESI): 321 (MH)+

The starting materials were prepared as follows:

4-Nitrobenzyl (7R,8S)-8-[(1R)-1-(tert-butyldimethylsilyloxy)ethyl]-5-[2-(4-nitrobenzyloxycarbonyl)-aminoethylthio]-9-oxo-1-azabicyclo[5.2.0]non-2,4-diene-2-carboxylate was prepared from 4-nitrobenzyl (7R,8S)-8-[(1R)-1-(tert-butyldimethylsilyloxy)ethyl]-5,9-dioxo-1-azabicyclo[5.2.0] non-2-ene-2-carboxylate by using a similar procedure to that described in Example 2 except 2-[4-nitrobenzyloxycarbonyl-amino]ethanethiol was used instead of methylmercaptan.

1H NMR (400 MHz, CDCl3) δ:0.03 (s, 3H); 0.07 (s, 3H); 0.84 (s, 9H); 1.27 (d, 3H); 2.67 (ddd, 1H); 2.79 (dd, 1H); 2.88 (d, 1H); 2.97 (t, 2H); 3.45 (d, 1H); 3.49 (d, 1H); 3.61 (d, 1H); 4.29 (m, 1H); 5.20 (brs, 2H); 5.31 (d, 1H); 5.38 (d, 1H); 5.80 (d, 1H); 6.24 (d, 1H); 7.50 (d, 2H); 7.60 (d, 2H); 8.20–8.23 (m, 4H).

MS (ESI): 727 (MH)+

4-Nitrobenzyl (7R,8S)-8-[(1R)-1-hydroxyethyl]-5-[2-(4-nitrobenzyloxy-carbonyl)aminoethylthio]-9-oxo-1-azabicyclo[5.2.0]non-2,4-diene-2-carboxylate was prepared from 4-nitrobenzyl (7R,8S)-8-[(1R)-1-(tert-butyldimethylsilyloxy)]ethyl]-5-[2-(4-nitrobenzyloxycarbonyl)aminoethyl]thio-9-oxo-1-azabicyclo[5.2.0]non-2,4-diene-2-carboxylate by a similar procedure described in Example 1, method B.

1H NMR (400 MHz, CDCl3): δ1.37 (d, 3H); 2.71 (ddd, 1H); 2.85 (dd, 1H); 2.91–3.02 (m, 3H); 3.40–3.49 (m, 2H); 3.69 (d, 1H); 4.33 (m, 1H); 5.19 (brs, 2H); 5.32 (d, 1H); 5.37 (d, 1H); 5.90 (d, 1H); 6.26 (d, 1H); 7.50 (d, 2H); 7.59 (d, 2H); 8.22 (d, 4H).

EXAMPLE 5

(7R,8S)-5-(2-Aminoethylsulphonyl)-8-[(1R)-1-hydroxyethyl]-9-oxo-1-azabicyclo[5.2.0]non-2,4-diene-2-carboxylic acid

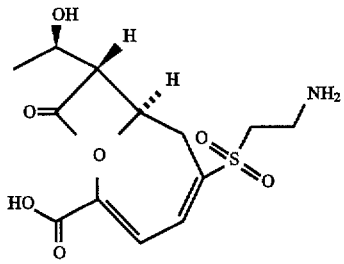

The title compound was prepared from 4-nitrobenzyl (7R,8S)-8-[(1R)-1-hydroxyethyl]-5-[2-(4-nitrobenzyloxycarbonyl)-aminoethylsulphonyl]-9-oxo-1-azabicyclo[5.2.0]non-2,4-diene-2-carboxylate by a similar procedure to that described in Example 1, method B.

1H NMR (400 MHz, D2O) δ:1.34 (d, 3H); 2.87 (ddd, 1H); 3.28 (dd, 1H); 3.41 (t, 2H); 3.49 (d, 1H); 3.63 (t, 2H); 3.82 (m, 1H); 4.38 (m, 1H); 5.78 (d, 1H); 7.18 (ddd, 1H).

The starting materials were prepared as follows:

4-Nitrobenzyl (7R,8S)-8-[(1R)-1-(tert-butyldimethylsilyloxy)ethyl]-5-[2-(4-nitrobenzyloxycarbonyl)aminoethylsulphonyl]-9-oxo-1-azabicyclo[5.2.0]non-2,4-diene-2-carboxylate was prepared from 4-nitrobenzyl (7R,8S)-8-[(1R)-1-(tert-butyldimethylsilyloxy)ethyl]-5-[2-(4-nitrobenzyloxycarbonyl) aminoethylthio]-9-oxo-1-azabicyclo[5.2.0]non-2,4-diene-2-carboxylate by using a similar procedure to that described in Example 3.

1H NMR (400 MHz, CDCl3) δ:0.02 (s, 3H); 0.07 (s, 3H); 0.82 (s, 9H); 1.28 (d, 3H); 2.62 (m, 1H); 3.00 (m, 1H); 3.19–3.25 (m, 2H); 3.52 (d, 1H); 3.60–3.76 (m, 3H); 4.23 (m, 1H); 5.19 (s, 2H); 5.38 (s, 2H); 5.48 (m, 1H); 6.12 (d, 1H); 7.12 (dd, 1H); 7.49 (d, 2H); 7.59 (d, 2H); 8.22 (d, 2H); 8.23 (d, 2H).

4-Nitrobenzyl (7R,8S)-8-[(1R)-1-hydroxyethyl]-5-[2-(4-nitrobenzyloxycarbonyl)aminoethylsulphonyl]-9-oxo-1-azabicyclo[5.2.0]non-2,4-diene-2-carboxylate was prepared from 4-nitrobenzyl (7R,8S)-8-[(1R)-1-(tert-butyldimethylsilyloxy)ethyl]-5-[2-(4-nitrobenzyloxycarbonyl)aminoethylsulphonyl]-9-oxo-1-azabicyclo[5.2.0]non-2,4-diene-2-carboxylate by a similar procedure to that described in Example 1, method B.

1H NMR (400 MHz, CDCl3+AcODd3)δ:1.38 (d, 3H); 2.70 (ddd, 1H); 3.08 (dd, 1H); 3.22–3.37 (m, 2H); 3.59–3.62 (m, 2H); 3.80 (dd, 1H); 4.35 (m, 1H); 5.18 (brs, 2H); 5.36 (d, 1H); 5.41 (d, 1H); 6.20 (d, 1H); 7.12 (dd, 1H); 7.49 (d, 2H); 7.59 (d, 2H); 8.20–8.25 (m, 4H).

We claim:
1. A compound of the formula (I):

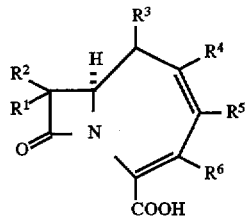

wherein:

R$^1$ is hydrogen or an optionally substituted group selected from acylamino, C$_{1-6}$alkyl, C$_{2-6}$alkenyl, C$_{2-6}$alkynyl, C$_{1-6}$alkoxy, C$_{1-6}$alkanoyloxy, C$_{1-6}$alkylamino, DI-(C$_{1-6}$alkyl)amino, C$_{1-6}$alkoxycarbonyl, aminocarbonyl, C$_{1-6}$alkylaminocarbonyl and DI-(C$_{1-6}$alkyl)aminocarbonyl;

R$^2$ is hydrogen or C$_{1-6}$alkoxy; or

R$^1$ and R$^2$ together form an optionally substituted C$_{1-6}$alkylene;

R$^3$ and R$^5$ are independently hydrogen or C$_{1-6}$alkyl; and one of R$^4$ and R$^6$ is hydrogen or C$_{1-4}$alkyl and the other is hydrogen, cyano, C$_{1-4}$alkylcarbonyl, C$_{1-4}$alkoxycarbonyl, benzoyl, C$_{1-4}$alkylsulphonyl, benzylsulphonyl, nitro, chloro, bromo, optionally substituted C$_{1-10}$alkyl, optionally substituted aryl, or a group of the formula —SR$^7$ wherein R$^7$ is an optionally substituted group selected from C$_{1-10}$alkyl, C$_{2-6}$alkenyl, C$_{2-6}$alkynyl, C$_{3-10}$cycloalkyl, C$_{3-10}$cycloalkylC$_{1-3}$alkyl, aryl, arylC$_{1-3}$alkyl, heterocyclyl, heterocyclylC$_{1-3}$alkyl, heteroaryl and heteroarylC$_{1-3}$alkyl; or one of R$^4$ and R$^6$ is hydrogen or C$_{1-4}$alkyl and the other is a group of the formula —OR$^{18}$, wherein R$^{18}$ is hydrogen or an optionally substituted group selected from C$_{1-6}$alkyl, aryl, C$_{1-6}$alkanoyl and arylcarbonyl; or one of R$^4$ and R$^6$ is hydrogen or C$_{1-4}$alkyl and the other is a group of the formula —N(R$^{19}$)R$^{20}$ wherein R$^{19}$ and R$^{20}$ are independently hydrogen or an optionally substituted group selected from C$_{1-6}$alkyl, C$_{1-6}$alkanoyl, arylC$_{1-3}$alkanoyl, arylcarbonyl, heterocyclyl, heterocyclylC$_{1-3}$alkyl, heteroaryl, heteroarylC$_{1-3}$alkyl, arylC$_{1-3}$alkyl, cycloalkyl and cycloalkylC$_{1-3}$alkyl; or one of R$^4$ and R$^6$ is hydrogen or C$_{1-4}$alkyl and the other is a group of the formula —CH$_2$R$^{21}$ wherein R$^{21}$ is aryl, or is a group selected from the formulae —SR$^7$, —OR$^{18}$ and —N(R$^{19}$)R$^{20}$ wherein R$^7$, R$^{18}$, R$^{19}$ and R$^{20}$ are as hereinabove defined;

wherein any heteroaryl is selected from the group consisting of an optionally substituted 5- or 6-membered mono- or 8–10 membered bi-aromatic ring structure having 1–4 ring heteroatoms selected from nitrogen, oxygen and sulphur; and any heterocyclyl is selected from the group consisting of an optionally substituted, saturated or partially saturated, 5- or 6-membered mono- or 8–10 membered bicyclic ring system having 1–4 ring heteroatoms selected from nitrogen, oxygen and sulphur;

or a pharmaceutically acceptable salt thereof, or an in vivo hydrolysable ester thereof.

2. A compound according to claim 1 wherein R$^1$ is C$_{1-6}$alkyl optionally substituted by halo, hydroxy, C$_{1-6}$alkylthio, C$_{1-6}$alkanoyl, C$_{1-6}$alkylsulphinyl, C$_{1-6}$akylsulphonyl, triazolyl or tetrazolyl, or R$^1$ is acylamino.

3. A compound according to claim 1 or claim 2 wherein $R^2$ is hydrogen.

4. A compound according to claim 1 or claim 2 wherein $R^3$ is hydrogen or methyl.

5. A compound according to claim 1 or claim 2 wherein $R^5$ is hydrogen.

6. A compound of the formula (I):

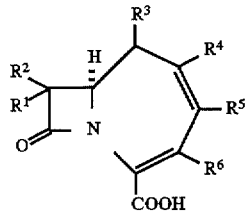

wherein:
$R^1$ is hydrogen or an optionally substituted group selected from acylamino, $C_{1-6}$alkyl, $C_{2-6}$alkenyl, $C_{2-6}$alkynyl, $C_{1-6}$alkoxy, $C_{1-6}$alkanoyloxy, $C_{1-6}$alkylamino, DI-($C_{1-6}$alkyl)amino, $C_{1-6}$alkoxycarbonyl, aminocarbonyl, $C_{1-6}$alkylaminocarbonyl and DI-($C_{1-6}$alkyl)aminocarbonyl;

$R^2$ is hydrogen or $C_{1-6}$alkoxy; or $R^1$ and $R^2$ together form an optionally substituted $C_{1-6}$alkylene;

$R^3$ and $R^5$ are independently hydrogen or $C_{1-6}$alkyl; and one of $R^4$ and $R^6$ is hydrogen and the other is hydrogen, optionally substituted $C_{1-10}$alkyl, optionally substituted aryl, a group of the formula —$S(O)_n R^7$ wherein n is 0, 1 or 2 and $R^7$ is an optionally substituted $C_{1-6}$alkyl or heterocyclyl group wherein:

optional substituents on the $C_{1-6}$alkyl are selected from amino, $C_{1-4}$alkylamino, DI-($C_{1-4}$alkyl)amino and groups of the formulae —N=C($R^8$)$R^9$, —N($R^{10}$)C($R^{11}$)=N—$R^{12}$ and —C(N($R^{13}$)$R^{14}$)=N—$R^{15}$ wherein $R^8$ is amino, $C_{1-4}$alkylamino or DI-($C_{1-4}$alkyl)amino and $R^9$, $R^{10}$, $R^{11}$, $R^{12}$, $R^{13}$, $R^{14}$ and $R^{15}$ are independently hydrogen or $C_{1-4}$alkyl, and optional substituents on the heterocyclyl group are selected from $C_{1-4}$alkyl, carboxy, $C_{1-4}$alkoxycarbonyl, —CON($R^{16}$)$R^{17}$ wherein $R^{16}$ is hydrogen or $C_{1-4}$alkyl and $R^{17}$ is hydrogen, $C_{1-4}$alkyl, aryl, heteroaryl, heterocyclyl, cycloalkyl and cycloalkyl$C_{1-3}$alkyl;

wherein any heteroaryl is selected from the group consisting of an optionally substituted 5- or 6-membered mono- or 8–10 membered bi-aromatic ring structure having 1–4 ring heteroatoms selected from nitrogen, oxygen and sulphur; and any heterocyclyl is selected from the group consisting of an optionally substituted, saturated or partially saturated, 5- or 6-membered mono- or 8–10 membered bicyclic ring system having 1–4 ring heteroatoms selected from nitrogen, oxygen and sulphur; or one of $R^4$ and $R^6$ is hydrogen and the other is a group of the formula —$OR^{18}$, wherein $R^{18}$ is hydrogen or an optionally substituted group selected from $C_{1-6}$alkyl, aryl, $C_{1-6}$alkanoyl and arylcarbonyl; or one of $R^4$ and $R^6$ is hydrogen and the other is a group of the formula —N($R^{19}$)$R^{20}$ wherein $R^{19}$ and $R^{20}$ are independently selected from hydrogen, $C_{1-4}$alkyl, $C_{1-4}$alkanoyl and aryl$C_{1-3}$alkyl; or one of $R^4$ and $R^6$ is hydrogen and the other is a group of the formula —$CH_2 R^{21}$ wherein $R^{21}$ is aryl, or is a group selected from the formulae —$SR^7$, —$OR^{18}$ and —N($R^{19}$)$R^{20}$ wherein R7, $R^{18}$, $R^{19}$ and $R^{20}$ are as hereinabove defined;

or a pharmaceutically acceptable salt thereof, or an in vivo hydrolysable ester thereof.

7. A compound according to claim 6 wherein $R^1$ is $C_{1-6}$alkyl optionally substituted by halo, hydroxy, $C_{1-6}$alkylthio, $C_{1-6}$alkanoyl, $C_{1-6}$alkylsulphinyl, $C_{1-6}$akylsulphonyl, triazolyl or tetrazolyl, or $R^1$ is acylamino.

8. A compound of the formula (I):

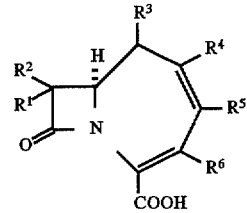

wherein:
$R^1$ is hydrogen or an optionally substituted group selected from acylamino, $C_{1-6}$alkyl, $C_{2-6}$alkenyl, $C_{2-6}$alkynyl, $C_{1-6}$alkoxy, $C_{1-6}$alkanoyloxy, $C_{1-6}$alkylamino, DI-($C_{1-6}$alkyl)amino, $C_{1-6}$alkoxycarbonyl, aminocarbonyl, $C_{1-6}$alkylaminocarbonyl and DI-($C_{1-6}$alkyl)aminocarbonyl;

$R^2$ is hydrogen or $C_{1-6}$alkoxy; or $R^1$ and $R^2$ together form an optionally substituted $C_{1-6}$alkylene;

$R^3$ and $R^5$ are independently hydrogen or $C_{1-6}$alkyl; and one of $R^4$ and $R^6$ is $C_{1-4}$alkanoyloxy or a group of the formula —$S(O)_n R^7$ wherein n is 0 or 2 and $R^7$ is $C_{1-6}$alkyl optionally substituted by amino; or one of $R^4$ and $R^6$ is of the formula —$SR^7$ wherein $R^7$ is of the formula:

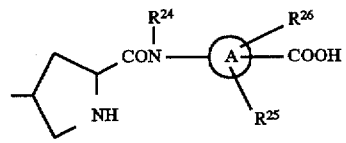

wherein $R^{24}$ is hydrogen or $C_{1-4}$alkyl and A is a phenyl or thienyl ring; and $R^{25}$ and $R^{26}$ are the same or different and are selected from hydrogen, halo, cyano, $C_{1-4}$alkyl, nitro, hydroxy, carboxy, $C_{1-4}$alkoxy, $C_{1-4}$alkoxycarbonyl, aminosulphonyl, $C_{1-4}$alkylaminosulphonyl, di-$C_{1-4}$alkylaminosulphonyl, carbamoyl, $C_{1-4}$alkylcarbamoyl, di-$C_{1-4}$alkylcarbamoyl, trifluoromethyl, sulphonic acid, amino, $C_{1-4}$alkylamino, di-$C_{1-4}$alkylamino, $C_{1-4}$alkanoylamino, $C_{1-4}$alkanoyl(N-$C_{1-4}$alkyl)amino, $C_{1-4}$alkanesulphonamido and $C_{1-4}$alkylS(O)$_n$— wherein n is 0, 1 or 2;

or a pharmaceutically acceptable salt thereof, or an in vivo hydrolysable ester thereof.

9. A compound selected from the group consisting of:
(7R,8S)-5-acetoxy-8-(1-hydroxyethyl)-9-oxo-1-azabicyclo[5.2.0]non-2,4-diene-2-carboxylic acid;
(7R,8S)-8-((1R)-1-hydroxyethyl)-5-methylthio-9-oxo-1-azabicyclo-[5.2.0]non-2,4-diene-2-carboxylic acid;
(7R,8S)-8-((1R)-1-hydroxyethyl)-5-methanesulphonyl-9-oxo-1-azabicyclo[5.2.0]non-2,4-diene-2-carboxylic acid;

(7R,8S)-5-(2-aminoethylthio)-8-((1R)-1-hydroxyethyl)-9-oxo-1-azabicyclo[5.2.0]-2,4-diene-2-carboxylic acid; and
(7R,8S)-5-(2-aminoethylsulphonyl)-8-((1R)-1-hydroxyethyl)-9-oxo-1-azabicyclo[5.2.0]-2,4-diene-2-carboxylic acid;
and pharmaceutically acceptable salts thereof.

10. A pharmaceutical composition comprising a pharmaceutically effective amount of a compound according to claim 1 and a pharmaceutically acceptable carrier.

11. A method of treating a bacterial infection in a warm blooded animal in need thereof, comprising administering to said animal an antibacterially effective amount of a compound according to claim 1.

12. A compound of the formula (II):

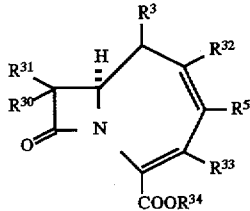

wherein $R^3$ and $R^5$ are independently hydrogen or $C_{1-6}$alkyl;
$R^{30}$ is an optionally substituted group selected from acylamino, $C_{1-6}$alkyl, $C_{2-6}$alkenyl, $C_{2-6}$alkynyl, $C_{1-6}$alkoxy, $C_{1-6}$alkanoyloxy, $C_{1-6}$alkylamino, DI-($C_{1-6}$alkyl)amino, $C_{1-6}$alkoxycarbonyl, aminocarbonyl, $C_{1-6}$alkylaminocarbonyl and DI-($C_{1-6}$alkyl)aminocarbonyl, which group is optionally protected;
$R^{31}$ is hydrogen or $C_{1-6}$alkoxy; or
$R^{30}$ and $R^{31}$ together form an optionally substituted $C_{1-6}$alkylene wherein any optional substituent is optionally protected;
$R^{32}$ and $R^{33}$ are optionally protected, and one of $R^{32}$ and $R^{33}$ is hydrogen or $C_{1-4}$alkyl and the other is hydrogen, cyano, $C_{1-4}$alkylcarbonyl, $C_{1-4}$alkoxycarbonyl, benzoyl, $C_{1-4}$alkylsulphonyl, benzylsulphonyl, nitro, chloro, bromo, optionally substituted $C_{1-10}$alkyl, optionally substituted aryl, or a group of the formula —$S(O)_nR^7$ wherein n is 0, 1 or 2 and $R^7$ is an optionally substituted group selected from $C_{1-10}$alkyl, $C_{2-6}$alkenyl, $C_{2-6}$alkynyl, $C_{3-10}$cycloalkyl, $C_{3-10}$cycloalkyl$C_{1-3}$alkyl, aryl, aryl$C_{1-3}$alkyl, heterocyclyl, heterocyclyl$C_{1-3}$alkyl, heteroaryl and heteroaryl$C_{1-3}$alkyl; or
one of $R^{32}$ and $R^{33}$ is hydrogen or $C_{1-4}$alkyl and the other is a group of the formula —$OR^{18}$, wherein $R^{18}$ is hydrogen or an optionally substituted group selected from $C_{1-6}$alkyl, aryl, $C_{1-6}$alkanoyl and arylcarbonyl; or
one of $R^{32}$ and $R^{33}$ is hydrogen or $C_{1-4}$alkyl and the other is a group of the formula —$N(R^{19})R^{20}$ wherein $R^{19}$ and $R^{20}$ are independently hydrogen or an optionally substituted group selected from $C_{1-6}$alkyl, $C_{1-6}$alkanoyl, aryl$C_{1-3}$alkanoyl, arylcarbonyl, heterocyclyl, heterocyclyl$C_{1-3}$alkyl, heteroaryl, heteroaryl$C_{1-3}$alkyl, aryl$C_{1-3}$alkyl, cycloalkyl and cycloalkyl$C_{1-3}$alkyl; or
one of $R^{32}$ and $R^{33}$ is hydrogen or $C_{1-4}$alkyl and the other is a group of the formula —$CH_2R^{21}$ wherein $R^{21}$ is aryl, or is a group selected from the formulae —$SR^7$, —$OR^{18}$ and —$N(R^{19})R^{20}$ wherein $R^7$, $R^{18}$, $R^{19}$ and $R^{20}$ are as hereinabove defined;
wherein any heteroaryl is selected from the group consisting of an optionally substituted 5- or 6-membered mono- or 8–10 membered bi-aromatic ring structure having 1–4 ring heteroatoms selected from nitrogen, oxygen and sulphur; and any heterocyclyl is selected from the group consisting of an optionally substituted, saturated or partially saturated, 5- or 6-membered mono- or 8–10 membered bicyclic ring system having 1–4 ring heteroatoms selected from nitrogen, oxygen and sulphur; and
—$COOR^{34}$ is carboxy or protected carboxy;
provided that said compound has at least one protecting group.

13. A compound of the formula (III)

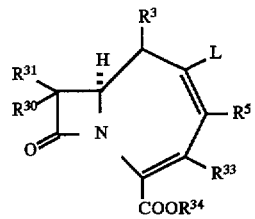

wherein $R^3$ and $R^5$ are independently hydrogen or $C_{1-6}$alkyl;
$R^{30}$ is an optionally substituted group selected from acylamino, $C_{1-6}$alkyl, $C_{2-6}$alkenyl, $C_{2-6}$alkynyl, $C_{1-6}$alkoxy, $C_{1-6}$alkanoyloxy, $C_{1-6}$alkylamino, DI-($C_{1-6}$alkyl) amino, $C_{1-6}$alkoxycarbonyl, aminocarbonyl, $C_{1-6}$alkylaminocarbonyl and DI-($C_{1-6}$alkyl)aminocarbonyl, which group is optionally protected;
$R^{31}$ is hydrogen or $C_{1-6}$alkoxy; or
$R^{30}$ and $R^{31}$ together form an optionally substituted $C_{1-6}$alkylene wherein any optional substituent is optionally protected;
$R^{33}$ is hydrogen or $C_{1-4}$alkyl;
—$COOR^{34}$ is carboxy or protected carboxy; and
L is a leaving group;
provided that said compound has at least one protecting group.

14. A compound of the formula (IIIA):

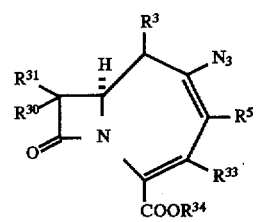

wherein $R^3$ and $R^5$ are independently hydrogen or $C_{1-6}$alkyl;
$R^{30}$ is an optionally substituted group selected from acylamino, $C_{1-6}$alkyl, $C_{2-6}$alkenyl, $C_{2-6}$alkynyl, $C_{1-6}$alkoxy, $C_{1-6}$alkanoyloxy, $C_{1-6}$alkylamino, DI-($C_{1-6}$alkyl)amino, $C_{1-6}$alkoxycarbonyl, aminocarbonyl, $C_{1-6}$alkylaminocarbonyl and DI-($C_{1-6}$alkyl)aminocarbonyl, which group is optionally protected;
$R^{31}$ is hydrogen or $C_{1-6}$alkoxy; or
$R^{30}$ and $R^{31}$ together form an optionally substituted $C_{1-6}$alkylene wherein any optional substituent is optionally protected;
$R^{33}$ is hydrogen or $C_{1-4}$alkyl; and
—$COOR^{34}$ is carboxy or protected carboxy;
provided that said compound has at least one protecting group.

* * * * *